(12) United States Patent
Crainich

(10) Patent No.: US 8,672,209 B2
(45) Date of Patent: Mar. 18, 2014

(54) LAPROSCOPIC STAPLER

(75) Inventor: Lawrence Crainich, Charlestown, NH (US)

(73) Assignee: Design Standards Corporation, Charlestown, NH (US)

( * ) Notice: Subject to any disclaimer, the term of this patent is extended or adjusted under 35 U.S.C. 154(b) by 223 days.

(21) Appl. No.: 13/035,854

(22) Filed: Feb. 25, 2011

(65) Prior Publication Data

US 2011/0204120 A1   Aug. 25, 2011

Related U.S. Application Data

(60) Provisional application No. 61/307,979, filed on Feb. 25, 2010.

(51) Int. Cl.
*A61B 17/068* (2006.01)

(52) U.S. Cl.
USPC ................ 227/180.1; 227/19; 227/178.1

(58) Field of Classification Search
USPC ..................... 227/180.1, 178.1, 19
See application file for complete search history.

(56) References Cited

U.S. PATENT DOCUMENTS

| | | | |
|---|---|---|---|
| 5,452,836 A * | 9/1995 | Huitema et al. | 227/176.1 |
| 5,465,894 A * | 11/1995 | Clark et al. | 227/175.1 |
| 5,597,107 A * | 1/1997 | Knodel et al. | 227/175.2 |
| 5,673,841 A * | 10/1997 | Schulze et al. | 227/175.1 |
| 5,692,668 A * | 12/1997 | Schulze et al. | 227/175.1 |
| 6,773,438 B1 * | 8/2004 | Knodel et al. | 606/139 |
| 6,821,273 B2 * | 11/2004 | Mollenauer | 606/28 |
| 7,278,563 B1 | 10/2007 | Green | |
| 7,434,715 B2 * | 10/2008 | Shelton et al. | 227/175.2 |
| 7,510,107 B2 | 3/2009 | Timm et al. | |
| 7,641,671 B2 | 1/2010 | Crainich | |
| 7,959,051 B2 * | 6/2011 | Smith et al. | 227/176.1 |
| 8,167,185 B2 * | 5/2012 | Shelton et al. | 227/175.1 |
| 8,172,124 B2 * | 5/2012 | Shelton et al. | 227/180.1 |
| 2005/0072827 A1 * | 4/2005 | Mollenauer | 227/180.1 |
| 2005/0178813 A1 * | 8/2005 | Swayze et al. | 227/176.1 |
| 2006/0025816 A1 * | 2/2006 | Shelton, IV | 606/215 |
| 2006/0175375 A1 * | 8/2006 | Shelton et al. | 227/176.1 |
| 2008/0308607 A1 * | 12/2008 | Timm et al. | 227/176.1 |
| 2010/0023026 A1 * | 1/2010 | Zeiner et al. | 606/144 |
| 2010/0191255 A1 * | 7/2010 | Crainich et al. | 606/142 |
| 2010/0191282 A1 * | 7/2010 | Harris et al. | 606/219 |
| 2011/0147434 A1 * | 6/2011 | Hueil et al. | 227/178.1 |

* cited by examiner

*Primary Examiner* — Brian D Nash
(74) *Attorney, Agent, or Firm* — Bachman & LaPointe, P.C.

(57) ABSTRACT

A surgical stapling and cutting method comprises: inserting tissue between jaws of a stapler/cutter end effector; closing the jaws; progressively ejecting staples from a first jaw, the progression being from an open distal end of the end effector toward a proximal end of the end effector; and drawing a blade through the tissue in a direction from the distal end toward the proximal end. Apparatus may be provided for performing the method.

14 Claims, 26 Drawing Sheets

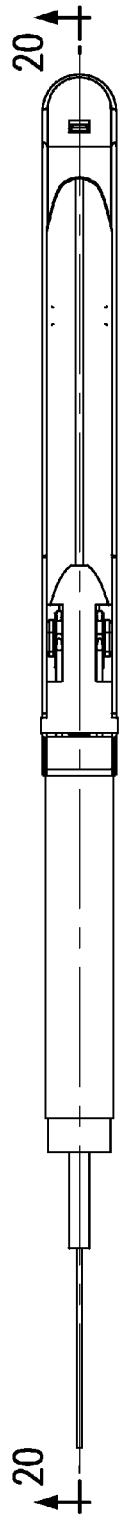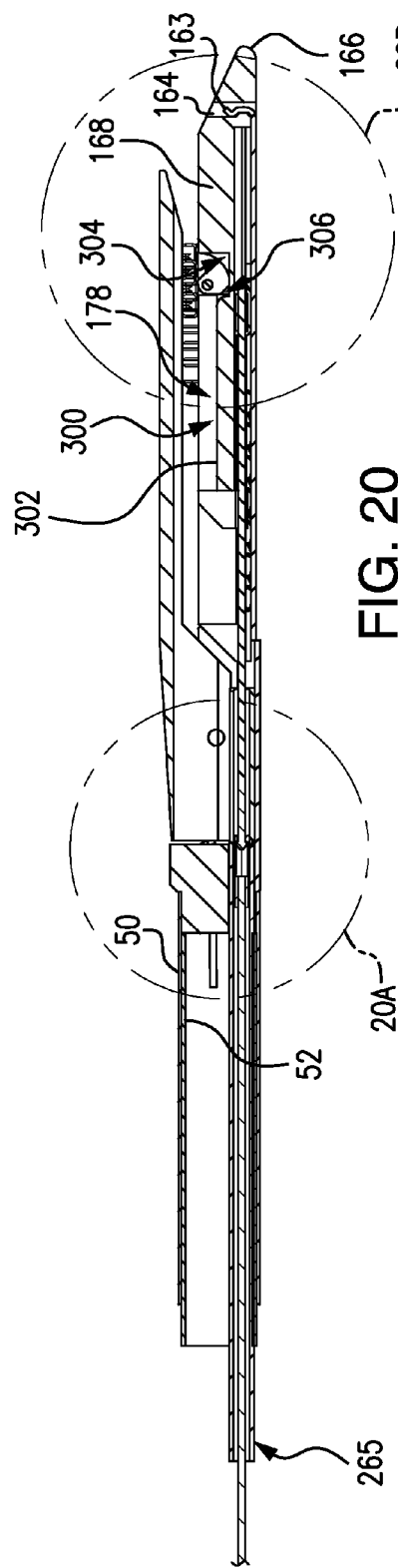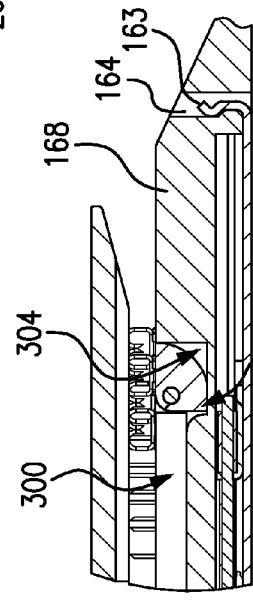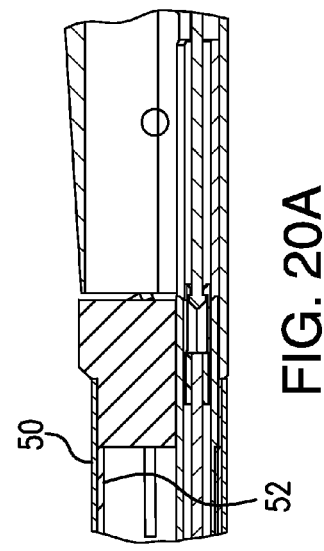
FIG. 19
FIG. 20
FIG. 20A
FIG. 20B

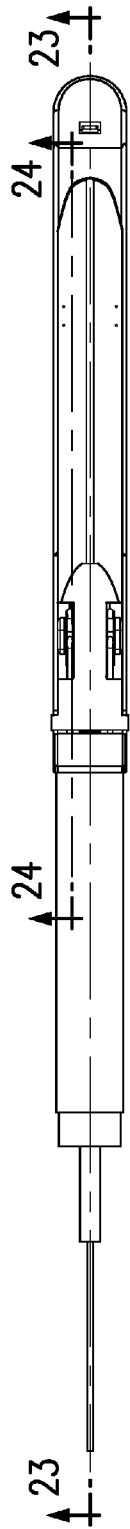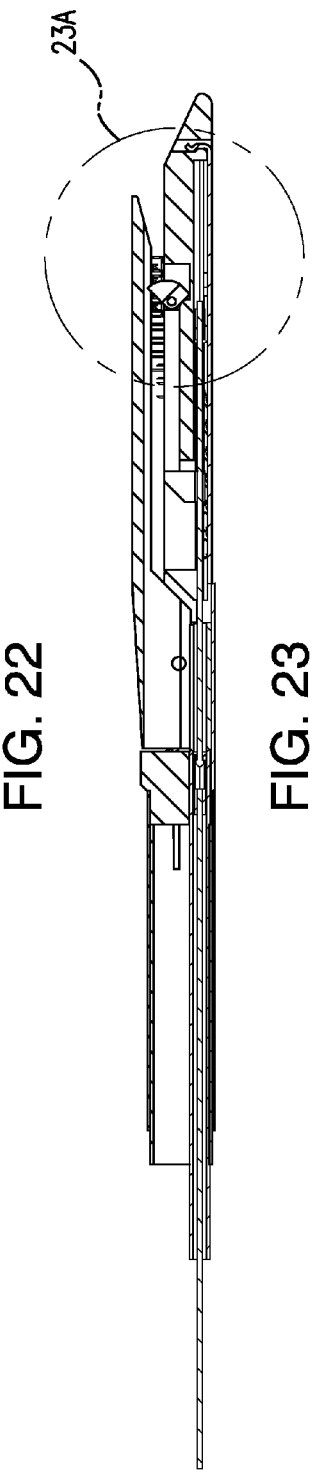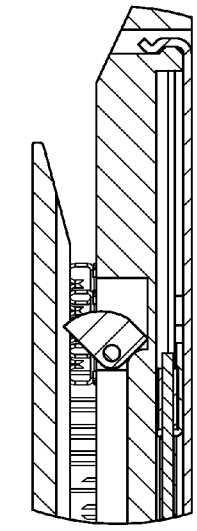
FIG. 22
FIG. 23
FIG. 23A
FIG. 24

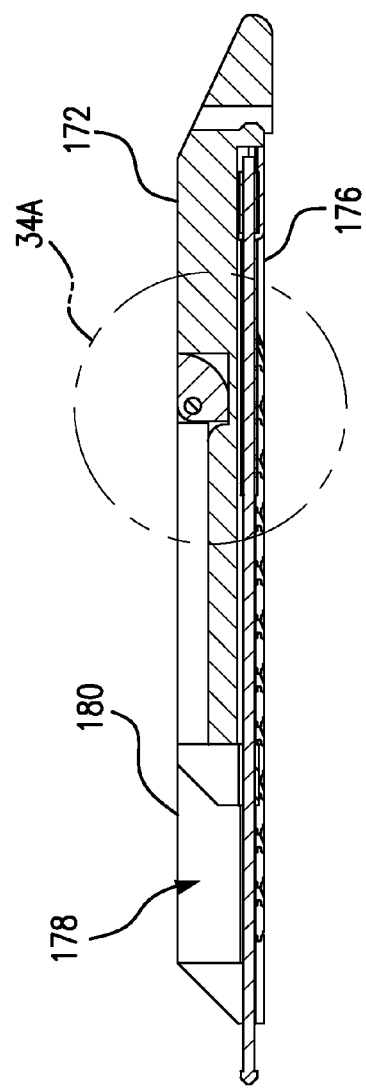
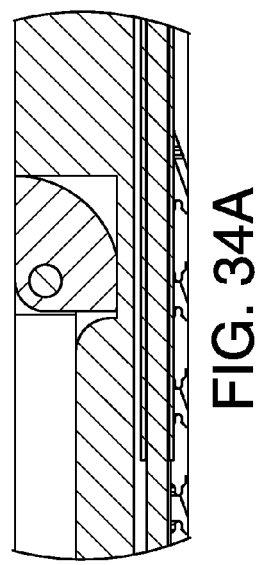
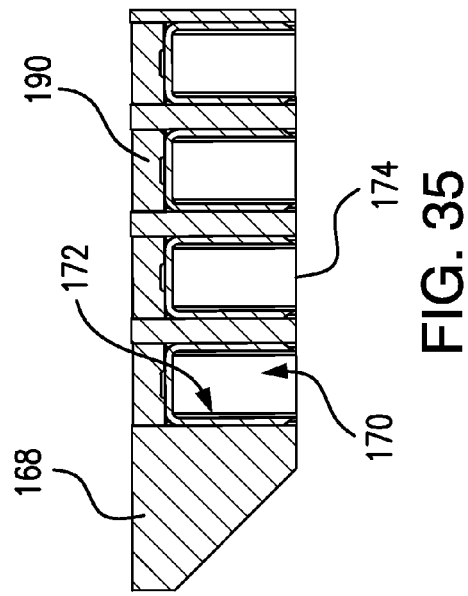

LAPROSCOPIC STAPLER

CROSS-REFERENCE TO RELATED APPLICATIONS

Benefit is claimed of U.S. patent application Ser. No. 61/307,979, filed Feb. 25, 2010, entitled "Laproscopic Stapler", the disclosure of which is incorporated by reference herein in its entirety as if set forth at length.

BACKGROUND OF THE INVENTION

The invention relates to surgical instruments. More particularly, the invention relates to combined surgical stapling/cutting devices.

Various surgical stapling/cutting devices have been proposed. Among these are devices shown in U.S. Pat. No. 7,278,563, U.S. Pat. No. 7,510,107, and U.S. Pat. No. 7,641,671.

SUMMARY OF THE INVENTION

One aspect of the invention involves a surgical stapler having an end effector and an actuator. The end effector has a staple cartridge holder and an anvil movable relative to the staple cartridge holder between open and closed positions. The actuator is coupled to the end effector to actuate the end effector from the open condition to the closed condition and drive the stapling. The actuator has a handgrip body and first and second levers. The levers are pivotable relative to the body from expanded conditions to contracted conditions and coupled to the end effector. Rotation of the first lever from its expanded condition to its contracted condition drives the end effector from its open condition to its closed condition. Rotation of the second lever from its expanded condition to its contracted condition drives the stapling.

Another aspect of the invention involves a surgical staple and blade cartridge having a cartridge body and a plurality of staples respectively accommodated in associated staple compartments of the cartridge body in an initial condition. A plurality of staple pushers are mounted in the body and positioned to be driven from an initial position to a second position. Movement from the initial position to the second position causes each staple pusher to drive one or more associated staples from their respective initial conditions outward toward fired conditions. A sled is positioned for sliding movement along the body from an initial position to a second position. The sled comprises a sled puller member having an end portion positioned so that pulling on the end portion tends to draw the sled from its initial position toward its second position. The sled has a plurality of ramps positioned to sequentially engage associated staple pushers as the sled is drawn from its initial position toward its second position. The engagement of the ramps to the associated staple pushers depresses the associated staple pushers from their respective initial positions to their respective second positions and, thereby, progressively ejects the associated staples. The tips of the staple pierce through tissue and are formed by the anvil that creates retention. A knife assembly has a blade puller member having a first end portion through which the sled puller passes. A blade is mounted to a second end portion of the blade puller member and has a cutting edge.

Another aspect of the invention involves a surgical stapling and cutting method comprising: inserting tissue between jaws of a stapler/cutter end effector; closing the jaws to clamp the tissue; progressively ejecting staples from a first jaw, the progression being from an open distal end of the end effector toward a proximal end of the end effector; and drawing a blade through the tissue in a direction from the distal end toward the proximal end.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 19 is an isolated underside view of the end effector in an intermediate condition of staple firing prior to blade deployment for cutting (with cannula and cable portions cutaway straight).

FIG. 20 is a central vertical axial sectional view of the end effector of FIG. 19, taken line 20-20.

FIG. 20A is an enlarged view of a proximal portion of the end effector of FIG. 20.

FIG. 20B is an enlarged view of a knife blade area of the end effector of FIG. 20.

FIG. 22 is an underside view of the end effector in a further state of firing with the blade at an intermediate stage of deployment.

FIG. 23 is a central vertical axial sectional view of the end effector of FIG. 22, taken along line 23-23.

FIG. 23A is an enlarged view of the blade region of the end effector of FIG. 23.

FIG. 24 is a partial vertical axial sectional view of the end effector of FIG. 22, taken along line 24-24.

FIG. 34 is a central vertical axial sectional view of the cartridge of FIG. 33, taken along line 34-34.

FIG. 34A is an enlarged view of the blade region of the cartridge of FIG. 34.

FIG. 35 is a partial vertical axial sectional view of the cartridge of FIG. 33, taken along line 35-35.

As is noted above, the drawings reflect various artifacts of computer aided design (CAD) which would be interpreted as such by one of ordinary skill in the art. In addition to those and other straight cutaways, there are various suppressed elements and even-lined sectioning regardless of material in any further stitching or wire frame artifacts. Like reference numbers and designations in the various drawings indicate like elements.

DETAILED DESCRIPTION

Figure 1:
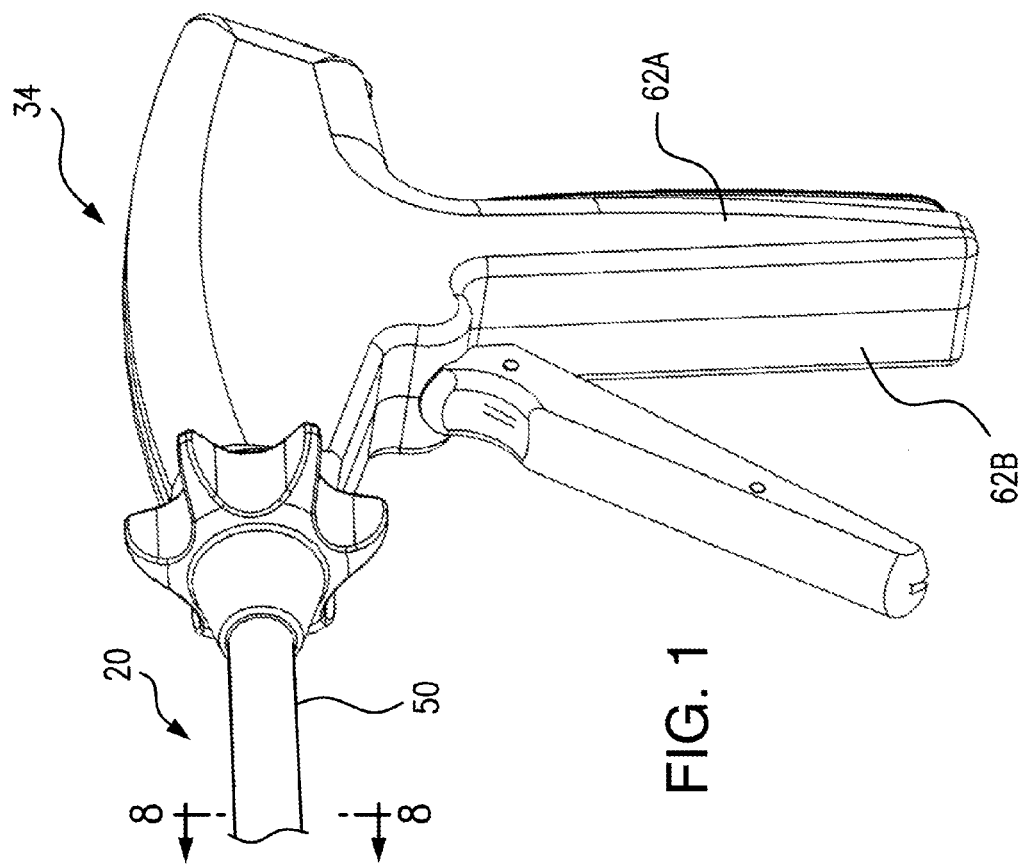
FIG. 1 is a view of an actuator of a laparoscopic stapler in a closed-jaw pre-firing condition.
Figure 2:
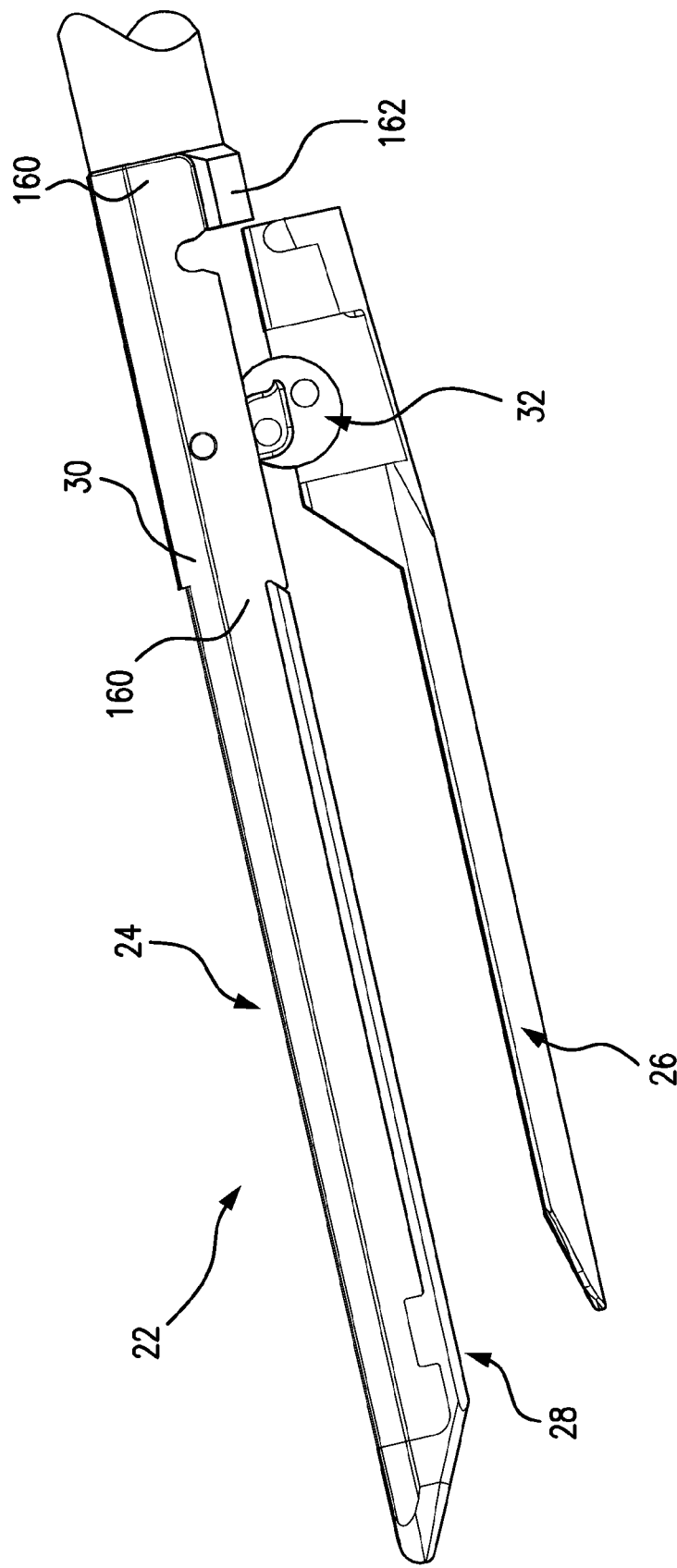
FIG. 2 is a view of an end effector of the stapler of FIG. 1 in an open jaw condition.
Figure 3:
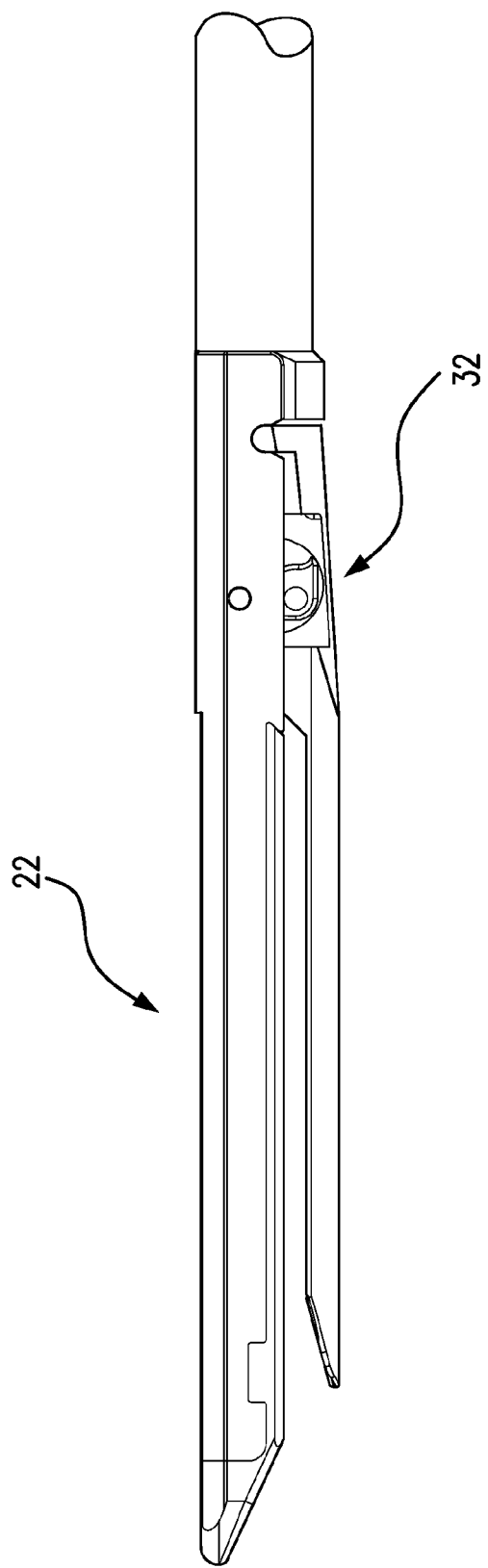
FIG. 3 is a view of the end effector in the closed-jaw pre-firing condition.

FIG. 1 shows a laparoscopic surgical stapler 20 having an actuator 34. An exemplary end effector 22 (FIG. 3) is a stapling and cutting end effector. The exemplary end effector 22 includes a first jaw 24 (FIG. 2) and a second jaw 26. The exemplary first jaw 24 (FIG. 2) is formed by a cartridge 28 and cartridge holder 30. The exemplary second jaw 26 is an anvil movable relative to the cartridge and holder between an open position (FIG. 2) and a closed position (FIG. 3). The exemplary cartridge 28 (FIG. 4 (see also, FIGS. 12 and 31-35)) is a disposable/replaceable combined surgical staple and blade cartridge. To guide movement between the open position and closed position, the jaws are coupled by linkage 32. An exemplary movement maintains parallel orientation of the jaws. An exemplary linkage 32 is drawn from U.S. Pat. No. 7,641,671 and the disclosure of which is incorporated by reference in its entirety herein as if set forth at length (hereafter the '671 patent). For ease of viewing, in many drawings, the actuator cables are not shown. As in the '671 patent, there may be a spring (not shown) biasing the jaws apart. Alternative linkages such as simple single-axis hinges, parallelogram mechanisms, and the like are possible.

An actuator 34 (FIG. 1) is coupled to the end effector to actuate the end effector from the open condition to the closed condition and drive the stapling and cutting.

The inventive actuator 34 (FIG. 5) has a first lever 40 (compressible to a FIG. 6 condition) for closing the end effector and a second lever 42 (compressible to a FIG. 7 condition) for firing the end effector (driving the stapling and the cutting). Although the inventive actuator may be used with the present inventive end effector, the inventive actuator may also be used with other end effectors. Although both the actuator and effector are illustrated in the context of a laparoscopic stapler, these may be independently or collectively implemented in non-laparoscopic devices.

Figure 8:
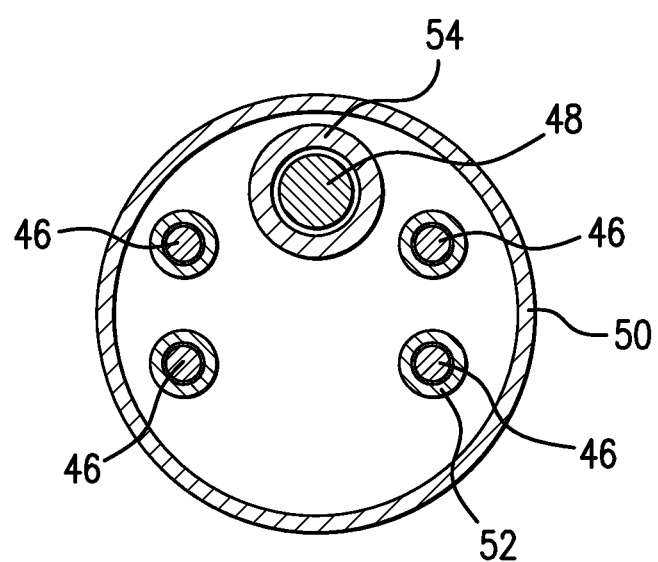
FIG. 8 is a sectional view of a cannula of the stapler.

The actuator 34 is coupled to the end effector 22 via flexible tension members for respectively actuating the end effector closing (46) and firing (48). The exemplary flexible tension members comprise metal cables. Alternative flexible tension members are metal wires or non-metallic equivalents. The exemplary cables 46 and 48 pass through a cannula or conduit 50 which is positioned to undergo a counter-compression when tension is applied by the levers to the cables. The exemplary conduit 50 is a single rigid stainless steel conduit passing the cables and there are jackets (FIG. 8) associated with the individual cables. Alternatively, the conduit may be flexible. Exemplary jackets are coil pipes 52, 54 which is a tightly wound spring configuration (like the body of an extension spring). The cables fit inside the coil pipes. With a rigid conduit 50, the exemplary jackets do not need to undergo compression; instead they serve to prevent cable kinking and distortion. In the situation of a flexible conduit, the individual cable jackets may be more likely configured to bear the compressive force of actuation.

Figure 5:
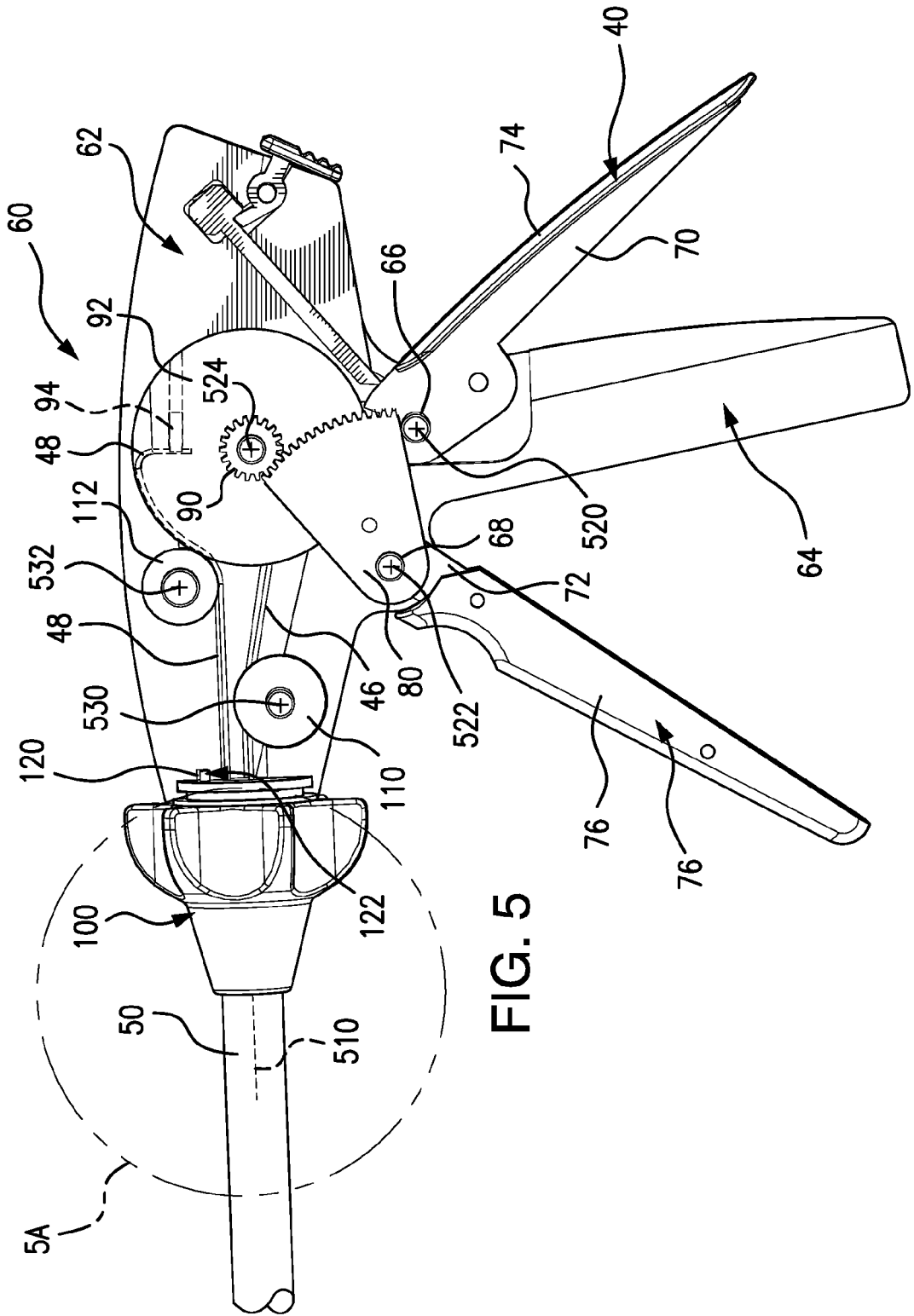
FIG. 5 is a view of an actuator of the stapler in an open-jaw pre-firing condition with a left body side removed.
Figure 6:
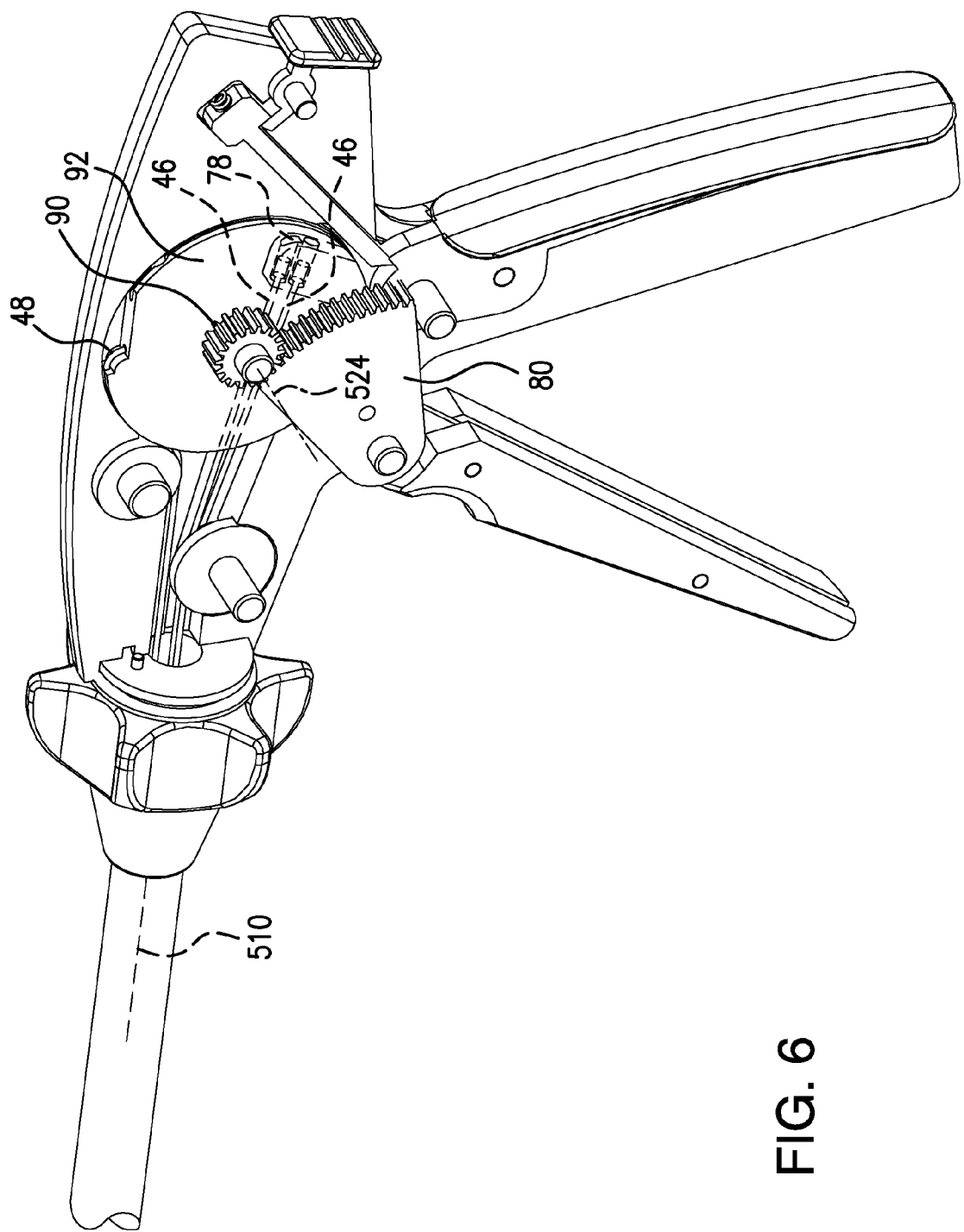
FIG. 6 is a view of the actuator in a closed-jaw pre-firing condition.
Figure 7:
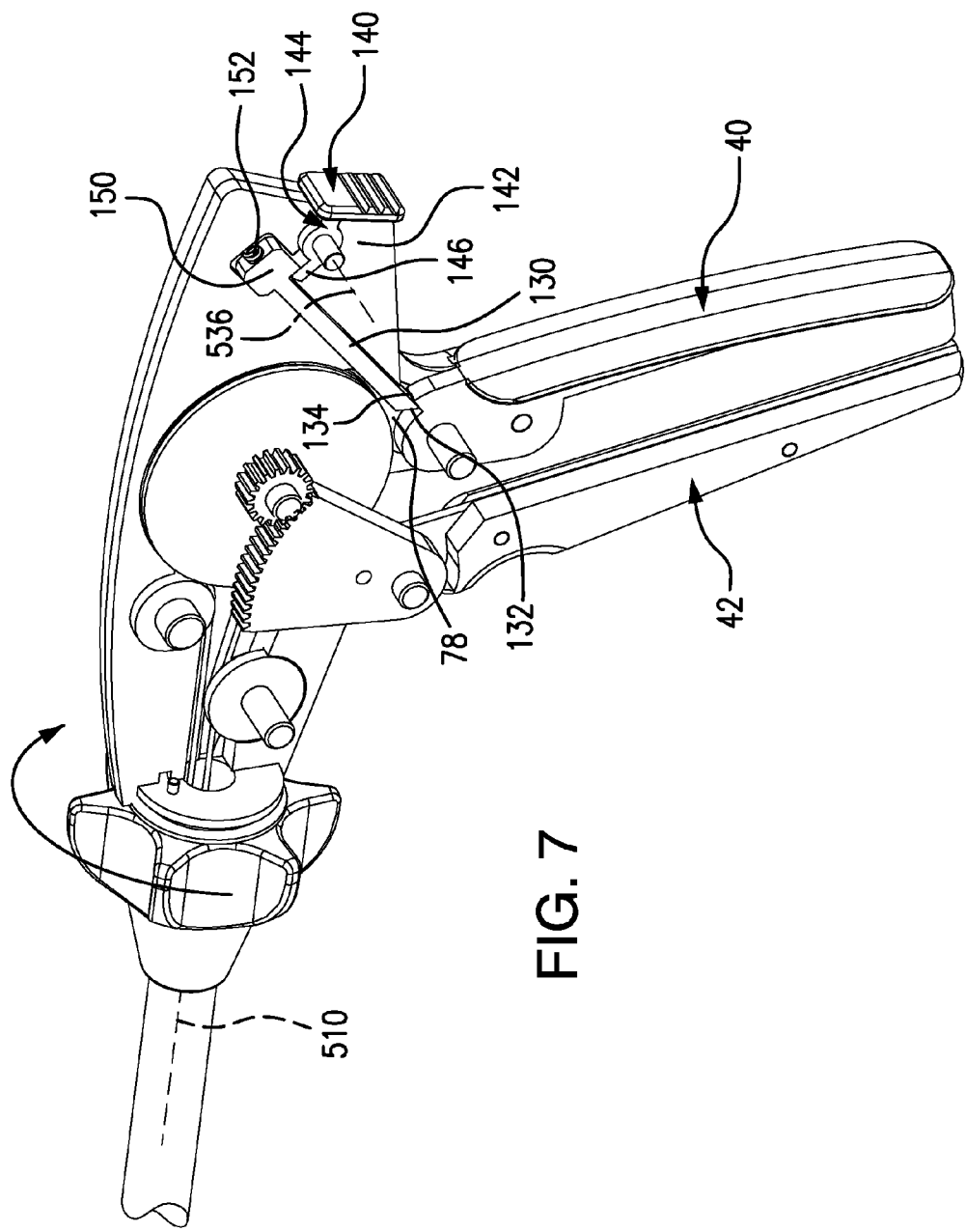
FIG. 7 is a view of the actuator in a closed-jaw fully fired condition.

The actuator includes a body 60 (FIG. 5) which further includes a main body 62 and a handgrip body 64 depending from the main body. The exemplary body 60 is formed from molded left and right halves 62A;62B (FIG. 1) assembled to each other. The exemplary first lever 40 is mounted to the body 60 for rotation about a first axis 520 (e.g., via a pivot pin 66). Similarly, the second lever 42 is mounted for rotation about a second axis 522 via a pin 68. Each of the levers 40 and 42 may itself be an assembly. As is shown, each of the levers includes a driving portion having a structural core 70;72 and an ergonomic grip 74;76. The structural portion 70;72 is secured to a driven portion 78;80 generally opposite. In an exemplary implementation, the first cable 46 (shown as a pair of first cables, laterally spaced apart to avoid creating yawing torques as is discussed below) is directly connected to the driven portion 78 (FIG. 6). The second cable 48 is coupled to the second lever via a gear mechanism. As part of the gear mechanism, the portion 80 is formed as a sector of a relatively large gear which is intermeshed with a relatively small pinion gear 90 rotatable about an axis 524. The pinion gear 90 is mounted to a spool 92 to which the second cable is mounted (e.g., via a set screw 94).

In the exemplary actuator, the cables pass through the central aperture of a rotation knob 100 (FIG. 5) which, in turn, is mounted to the conduit 50. In order to align the cables with the interior of the knob/rigid conduit combination, a pair of idler pulleys 110 and 112 are shown rotatable about respective axes 530 and 532. The knob 100 has a central axis 510 which forms an axis of rotation of the knob relative to the main body 60 and which is coincident with a centerline of the conduit 50. The rotation knob is rotatable about the axis 510 to, in turn, correspondingly rotate the end effector. The range of rotary motion of the knob may be constrained between first and second end points. Exemplary constraint is provided by a stop 120 on the rotation knob which passes through a slot 122 having portions in the respective left and right body halves. Interaction of the stop with the ends (not shown) of the slot defines the limited range of rotation. Exemplary limited range of rotation is 90° in either direction.

Figure 9:
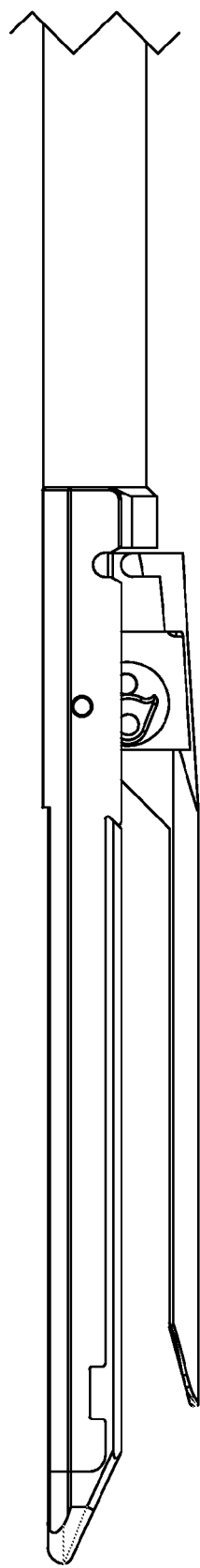
FIG. 9 is a view of the end effector in an intermediate condition of closure.

In an initial condition, the respective levers may be in relatively expanded conditions (i.e., away from the handle body 64: FIG. 5). The user may grip the handle body 64 and, with the palm of the user's hand depress the first lever to rotate it into its contracted condition (closer to/abutting the body 64: FIG. 6). As is discussed further below, this pulls on the first cable to close the end effector. As is discussed further below, FIG. 9 shows the end effector in an intermediate degree/stage of closing. When the first lever reaches its maximally contracted condition (or slightly shy thereof) a locking lever or latch/catch 130 (FIG. 7) having a distal pawl 132 may engage a complementary feature of the first lever (e.g., the recess 134 in the portion 78). The catch may be spring-loaded to bias it toward this locking contracted condition (FIG. 6). Accordingly, once the handle is depressed at least to a threshold condition, the handle will lock and not return to the initial condition.

As is discussed below, this may be done to grasp the tissue. However, in an exemplary use situation, this is initially done merely to contract the end effector to ease its insertion into the surgical site. After insertion, the end effector would then be opened to allow the end effector to acquire the tissue. To open the end effector, the catch may be released. An exemplary release is provided by depressing end portion 140 of a latch release 142. The end portion 140 is at one end of the driving portion 144 of a lever. A driven portion 146 opposite a release axis 536, in turn, engages the underside of a head 150 of the catch to lift the catch (against bias of the spring 152) out of engagement with the first lever, thereby allowing the first lever to rotate back to its expanded condition. Thereafter, the user may, with the fingers of his hand, pull the lever 76 to depress it from its expanded condition to its contracted condition (FIG. 7) to drive the stapling and cutting. The exemplary rotation of the lever 76 causes the portion 80 to rotate the pinion gear 90 and, in turn, rotate the spool 92 to pull the second cable to fire the stapler/knife. A compression spring (discussed below) in the sheath may return a collet assembly (discussed below) and cable to the original position. After firing, the end effector is opened as discussed above.

Figure 5A:
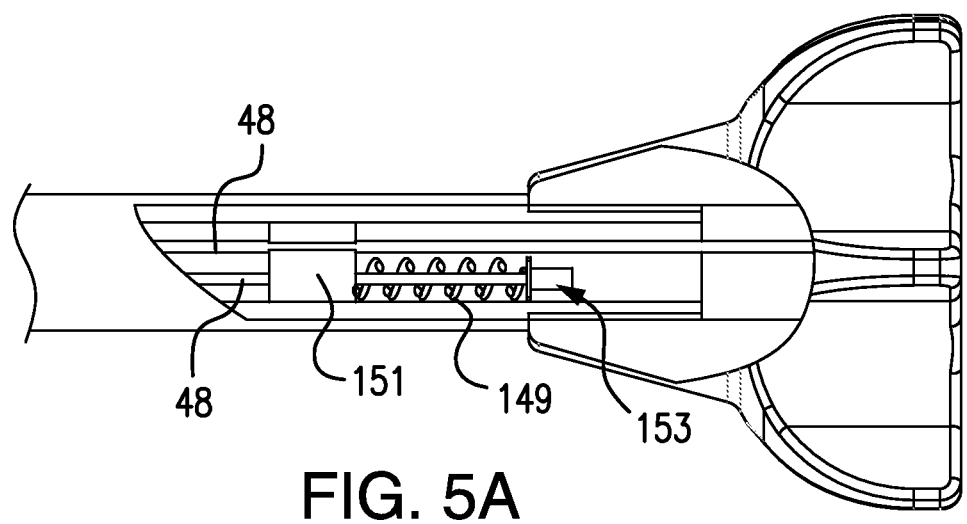
FIG. 5A is a cutaway view of a distal end of the actuator of FIG. 5.

A spring bias to open the jaws may be provided by a compression spring as in the prior '671 patent. Alternatively, each of the cables 46 may pass through the linkage 32 (being secured thereto) and extend to a second end which is held by a spring. One option (FIG. 5A) is a pair of compression springs 149 receiving end portions of the return legs of the two closing cables. Both legs (trigger and return) of each of the closing cables may pass freely through a support 151 within the conduit. The support is axially secured within the conduit. The proximal ends of the coil pipes for those four legs may abut or be near the downstream/distal face of the support (as may the proximal end of the coil pipe of the firing cable). The trigger legs of the cables pass through to the actuator. The return legs pass through and into the associated coil spring. A downstream end of each coil spring may abut an upstream end of the support. A terminal fixture 153 (e.g., a washer and crimped ferrule) at the end of the return leg may abut the upstream end of the spring. An alternative is a tension coil spring having a proximal end mounted within the conduit 50; either in common or one per cable). The tension spring(s) provide a return force to open the jaws. Alternatively, the two legs of each cable 46 could be replaced by separate closing and return cables. The use of left and right cables 46 prevents yawing torques which would be associated with a single off-center cable.

Figure 10:
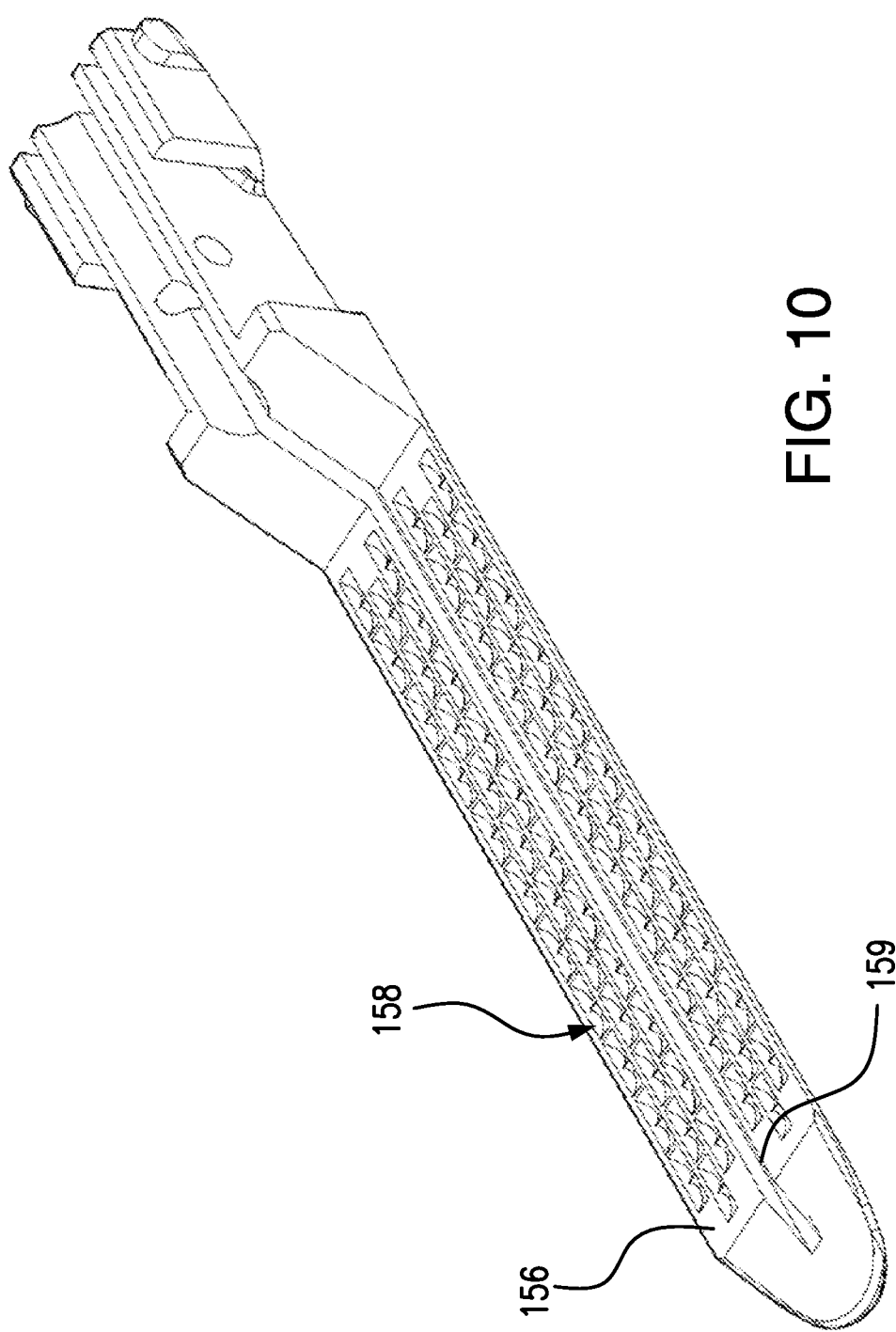
FIG. 10 is a view of an anvil jaw of the end effector.

The exemplary anvil has an inboard face 156 (FIG. 10) with a pair or arrays of pairs of staple crimping recesses 158 on respective sides of a cutting slot 159.

The exemplary cartridge holder 30 (FIG. 2) is formed of a sheet metal main portion 160 having a proximal end 161 secured to a connector 162 (e.g., machined metal) at the distal end of the conduit 50. The sheet metal portion 160 extends generally longitudinally. A distal end portion 163 (FIG. 11) of the main portion 160 is formed as an inwardly-bent finger which may be received in a corresponding aperture 164 near a distal end 166 of a cartridge body 168. The finger and aperture may be shaped to provide a removable detent locking of the distal end of the cartridge when the cartridge is installed to the holder (e.g., proximal end first inserted first and then rotated to engage the finger/slot).

Figure 4:
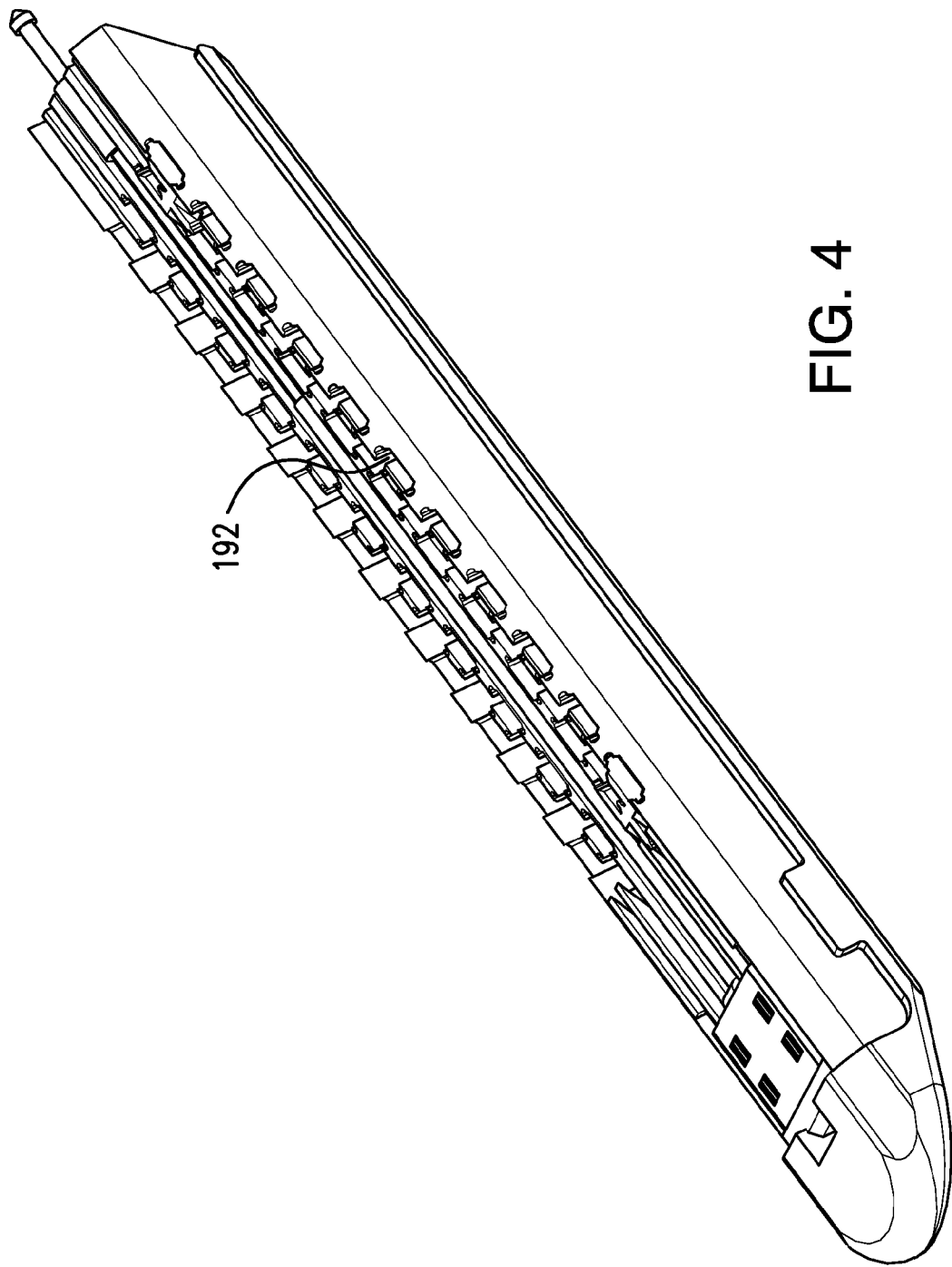
FIG. 4 is a view of a staple cartridge.
Figure 11:
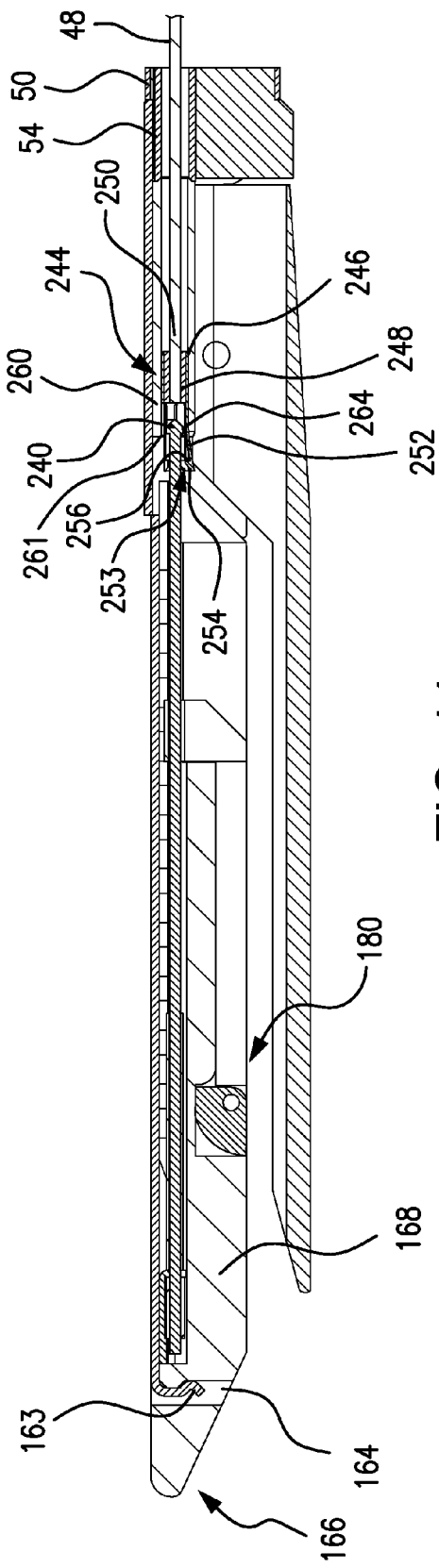
FIG. 11 is a central vertical axial sectional view of the end effector in the closed-jaw pre-firing condition.
Figure 12:
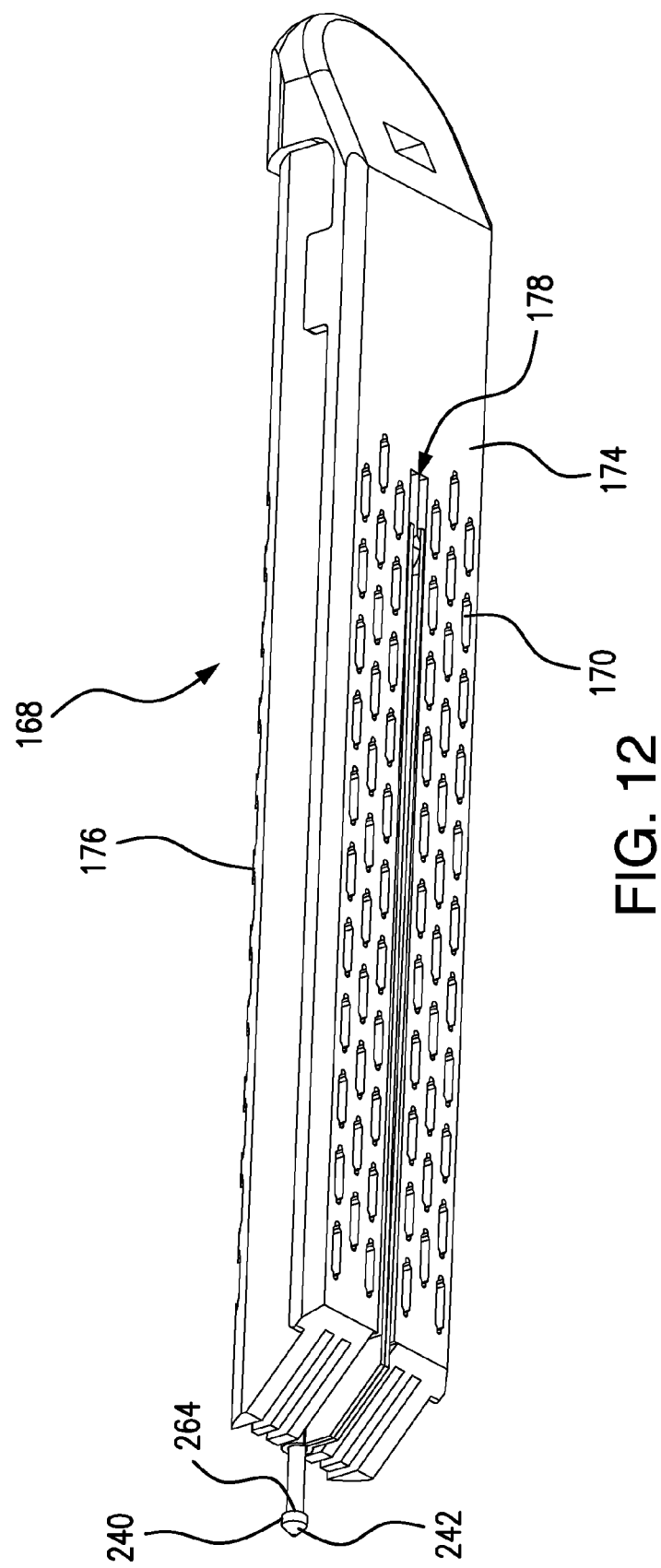
FIG. 12 is a second view of the stapler cartridge.
Figure 13:
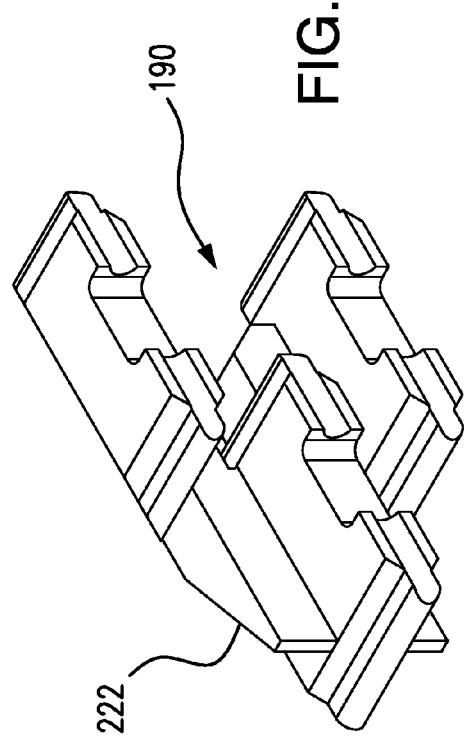
FIG. 13 is a view of a staple pusher.
Figure 14:
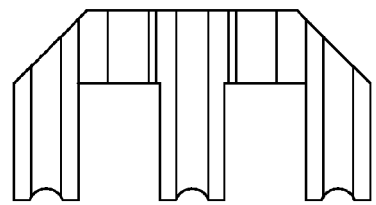
FIG. 14 is an end view of the stapler pusher.

The cartridge body 168 (FIG. 12) includes a plurality of staple compartments 170 each respectively accommodating an associated one of the plurality of staples 172 (discussed below) in an initial condition. The staple compartments 170 open to an inboard face 174 of the cartridge body. The cartridge body further includes an outboard face 176. The cartridge body further includes a central knife slot 178 which, as is discussed further below, accommodates a knife assembly 180 (FIG. 11). The exemplary cartridge body carries a first plurality of the staples on a first side of the knife assembly and a second plurality of the staples on a second side of the knife assembly. The exemplary staples of each of the pluralities are arranged in three rows with the staples oriented longitudinally and the adjacent rows offset exactly out of phase. The cartridge body further accommodates a plurality of staple pushers 190 (FIGS. 13-15) each mounted in an associated pusher compartment 192 (FIG. 4). Each exemplary pusher 190 is positioned to be driven from an initial position to a second position when movement from the initial position to the second position causes the pusher to drive one or more associated staples from their respective initial conditions outward toward fired conditions. In the exemplary embodiment, each pusher is positioned to engage a group of three staples (one from each associated row). Accordingly, the exemplary pushers are positioned with one row on the first side of the cartridge and a second row along the second side of the cartridge, the numbers of pushers per row being equal to the number of staples per staple row. Exemplary cartridge body and pusher materials are medical grade plastics of type commonly used for cartridge bodies and pushers.

Figure 15:
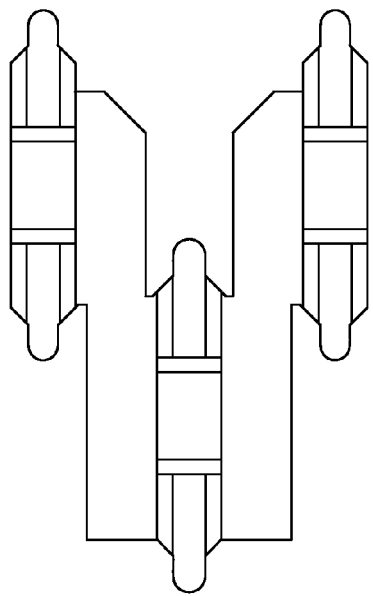
FIG. 15 is an underside view of the staple pusher.
Figure 16:
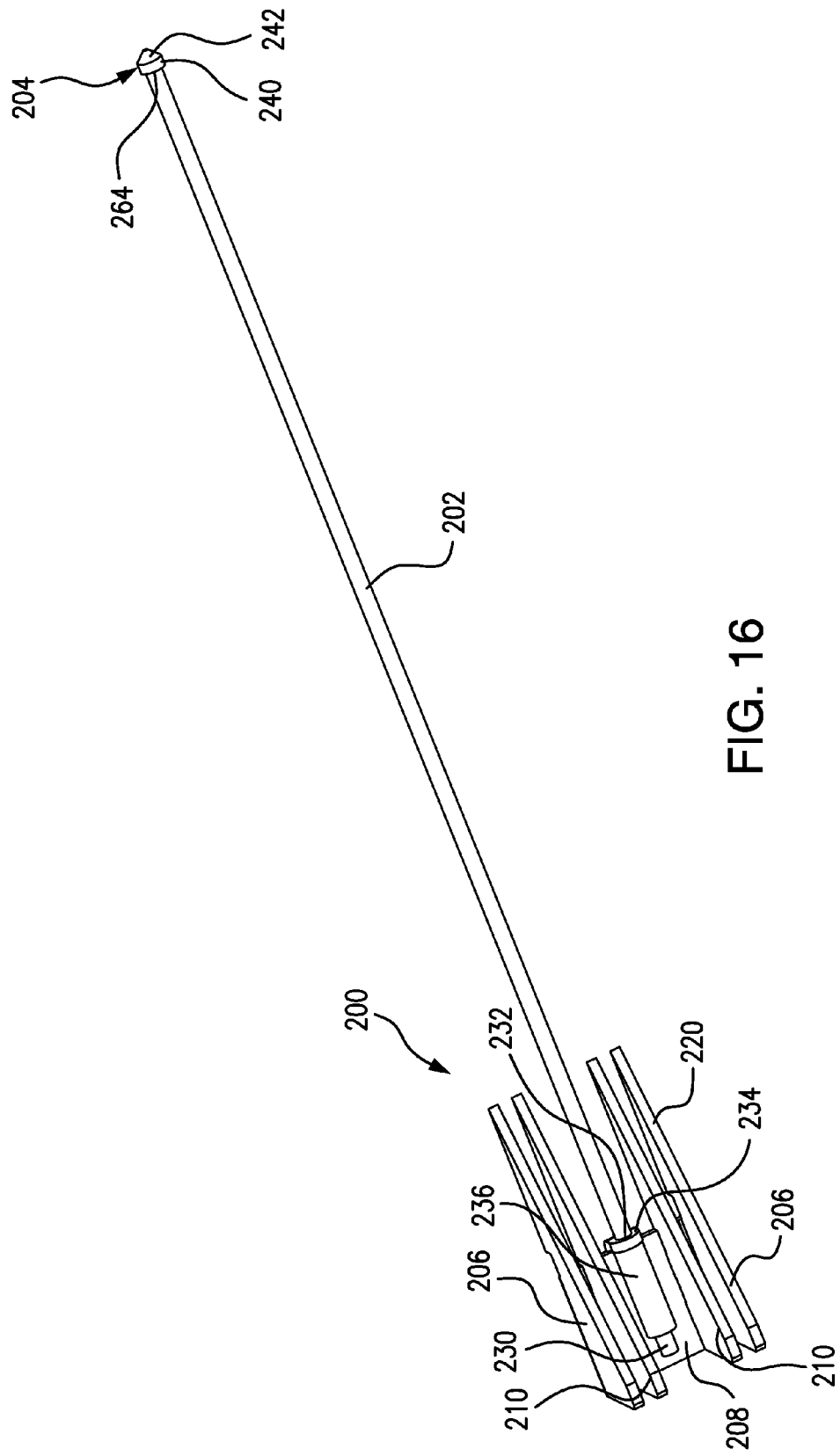
FIG. 16 is a view of a sled assembly for progressively depressing the staple pushers.

For driving the staples, a ramp sled 200 (FIG. 16) is positioned for sliding a movement along the cartridge body from an initial position to a second position. The ramp sled has a tension member (ramp/sled puller) 202 (e.g., a flexible wire) having an end portion 204 positioned so that pulling on the end portion tends to draw the ramp sled from its initial position toward its second position. The ramp sled includes a plurality of ramps. A first pair of the ramps are formed as outboard ramps 206 formed as peripheral portions of a sheet metal piece which also forms a web 208 of a sled body. A pair of inboard ramps 210 may be separately formed and secured to the web (e.g., via welding or staking). The ramps are positioned so that one outboard ramp and its adjacent inboard ramp sequentially engage the first plurality (row) of staple pushers while the other outboard ramp and inboard ramp sequentially engage the second plurality (row) of staple pushers as the ramp sled assembly is drawn from its initial position toward its second position. Each of the ramps has a ramping surface 220 positioned to engage an associated ramping surface 222 (FIG. 13) of the associated staple pushers so that, as the ramp passes over a staple pusher, the staple pusher is depressed from its initial position toward its second position, thereby driving the associated staples from their respective initial conditions outward toward their fired conditions to progressively eject the staples (discussed below). With the exemplary staple pushers, a pair of the ramping surfaces 222 on opposite sides of the staple pusher are respectively engaged by an associated inboard and outboard sled ramp. The exemplary staple pusher has three staple-engaging portions having end recesses for engaging the heads of the associated staples at approximate junctions with the legs of the staples. As is shown in FIG. 15, the central staple-engaging portion is exactly out of phase with the two outboard staple-engaging portions provide the stagger discussed above.

Exemplary sled assembly and knife assembly materials are medical grade stainless steel or other metals as are commonly used on surgical instruments.

The exemplary tension member 202 (FIG. 16) is formed as a flexible wire having a second end portion 230 opposite the first end portion 204. The second end portion 230 is mounted to the sled 200. The exemplary mounting involves the end portion 230 passing through an aperture 232 of a proximal end portion 234 of the sled body. A ferrule 236 is crimped over the second end portion 230 so that pulling on the tension member first end 204 causes the ferrule to apply force to the adjacent face of the portion 234 to draw the sled body along with the tension member 202.

Figure 17:
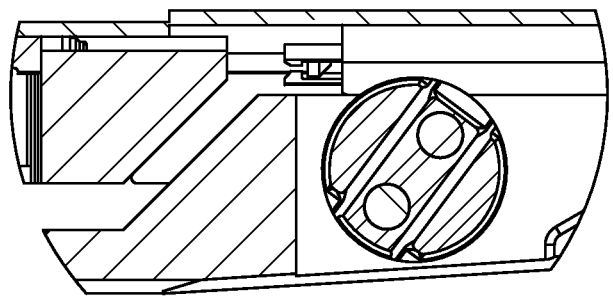
FIG. 17 is a vertical longitudinal sectional view of a portion of the end effector showing collet engagement to the sled.

The exemplary first end portion 204 is formed as an enlarged head 240 having a tapering end face 242. As is discussed further below, the head 240 may be captured by a collet 244 (FIG. 11) which, in turn, is connected to the second cable so that pulling of the second cable via the second lever draws the sled from its initial position toward the sled's second position. The exemplary collet 244 has a first end portion 246 mounted to a ferrule 248 which, in turn, is crimped to an end 250 of the second cable. The collet first end portion 246 may be crimped to the ferrule 248, welded to the ferrule 248, adhered to the ferrule 248 or the ferrule 248 may engage an end flange of the collet through which the cable passes. Alternatively, the collet and ferrule could be machined as a single piece. The second end of the collet is formed by a plurality of fingers 252 which have radially inward facing barbs 253. Each barb has an axially outward facing ramping surface 254 and axially inward facing underside 256. During cartridge installation the head 240 passes through the barbs into the collet. A pulling of the second cable will draw the collet into a collet closer 260 (e.g., a metallic tube having a distal end portion 261 through which the collet passes) which inwardly biases the fingers 252 to shift the fingers inward closer to the wire and brings the barb underside 256 axially closer to the head underside 264. Eventually, the barb undersides engage the head underside (FIG. 17) and begin to axially draw the wire along with the second cable to shift the sled as previously discussed. The collet may return to its initial position when the spent cartridge is withdrawn manually.

Figure 18:
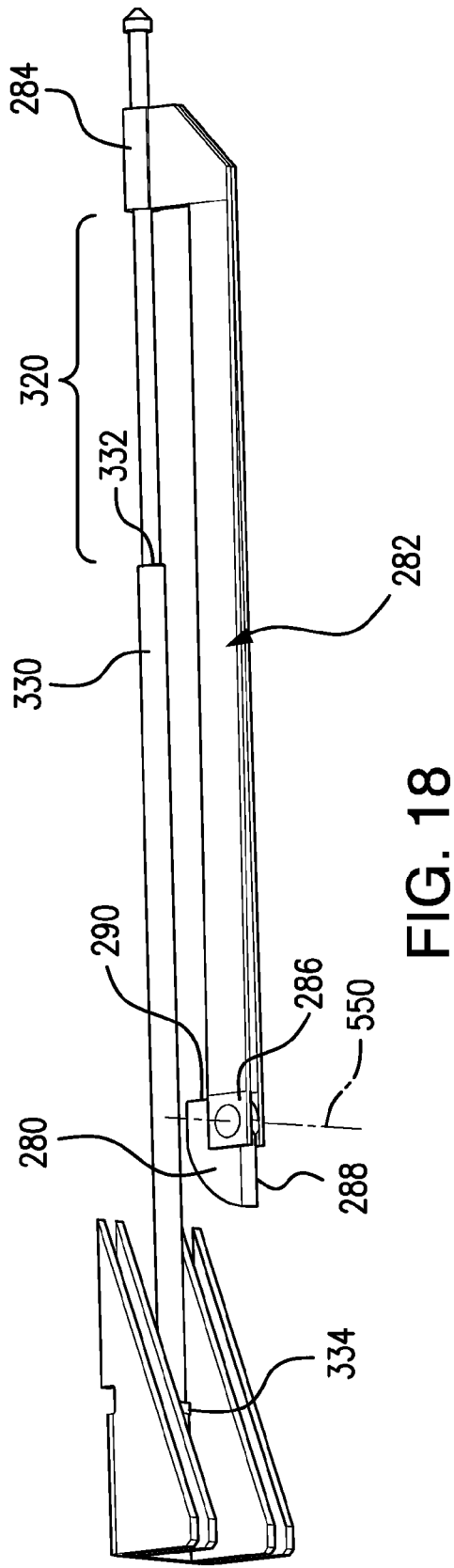
FIG. 18 is a view of a combined assembly of the sled assembly and a knife assembly.
Figure 21:
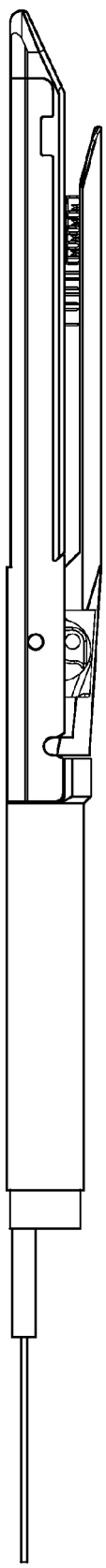
FIG. 21 is a side view of the end effector of FIG. 19.
Figure 25:
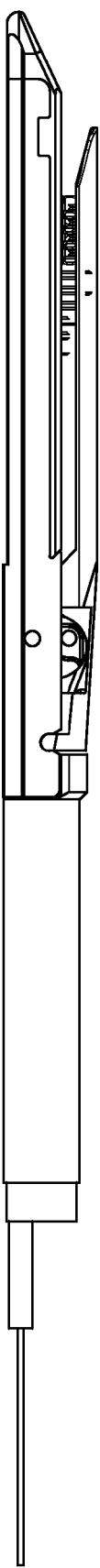
FIG. 25 is a side view of the end effector of FIG. 22.
Figure 27:
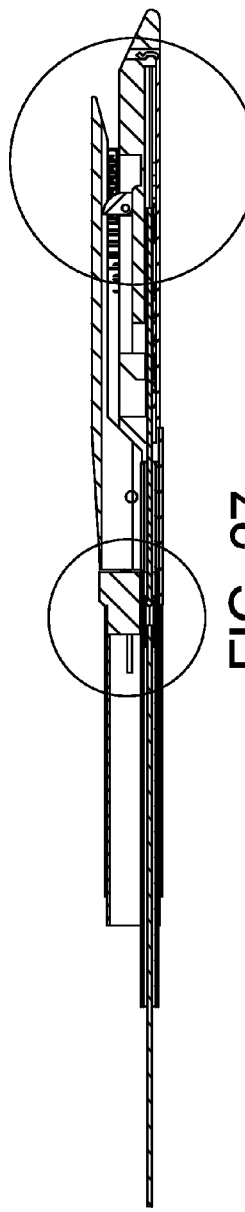
FIG. 27 is a vertical axial sectional view of the end effector of FIG. 26.
Figure 27B:
FIG. 27B is an enlarged view of the blade region.

As previously noted, the pulling of the second cable also drives the cutting operation. With the exemplary cartridge, the cutting operation begins only after the stapling has begun so that tissue is cut only after the adjacent portions of the tissue have been stapled. The exemplary knife assembly (FIG. 18) comprises a blade 280 and a blade puller member 282. The blade puller has a first end portion 284 through which the ramp puller wire 202 passes. The blade puller member has a second end portion 286 to which the blade is mounted. The blade has a cutting edge 288. The exemplary blade is pivotally mounted to the blade puller second end portion for rotation about an axis 550. In the initial condition, the cutting edge 288 is approximately parallel to and flush or slightly subflush to the inboard surface of the cartridge. The blade has a second edge 290 (FIG. 18) approximately perpendicular to the cutting edge 288. The exemplary knife slot 178 (FIG. 19) has a main portion 300 extending inward from the cartridge body inboard surface to a slot base 302. The blade is initially accommodated in a deeper end portion 304 of the knife slot with a shoulder surface 306 approximately normal to the base. With the knife in its initial condition, the shoulder 306 is in contacting or close facing relationship to the blade second edge 290. Pulling on the tension member causes engagement between the second edge 290 and the shoulder 306 to pivot the blade about the axis 550. This deploys the cutting edge to protrude (FIG. 23) from the cartridge inboard surface, initially penetrating the clamped tissue. Further movement rotates the blade into a full cutting orientation (FIG. 27, e.g., with the cutting edge approximately normal to the cartridge inboard surface) with the second edge 290 along the slot base. An exemplary rotation is 90+/−5°, more broadly 45-120° or 80-110°. In the cutting orientation, a tip portion of the blade 280 is accommodated within the anvil slot 159. Further pulling draws the blade along the tissue to perform the cutting/incision.

Figure 26:
FIG. 26 is an underside view of the end effector in a further state of firing with the blade just fully deployed.
Figure 28:
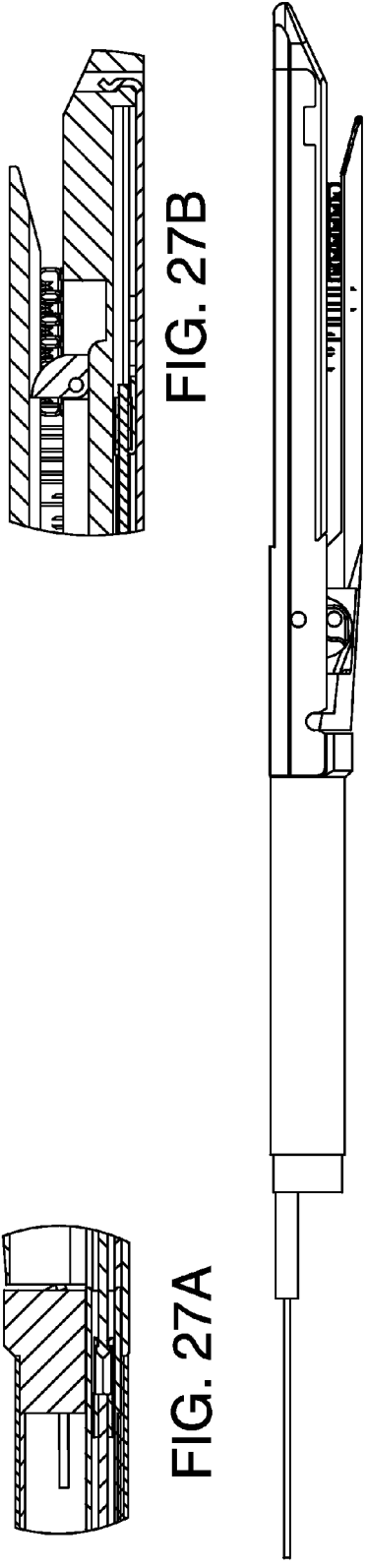
FIG. 28 is a side view of the end effector of FIG. 26.
Figure 27A:
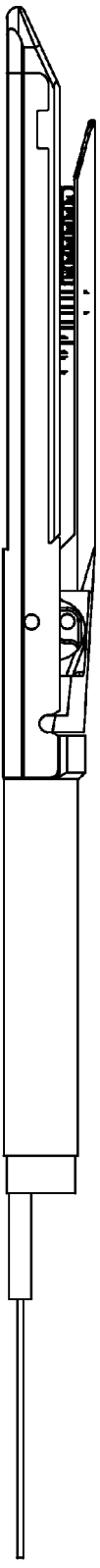
FIG. 27A is a view of the end effector-to-cannula interface.
Figure 29:
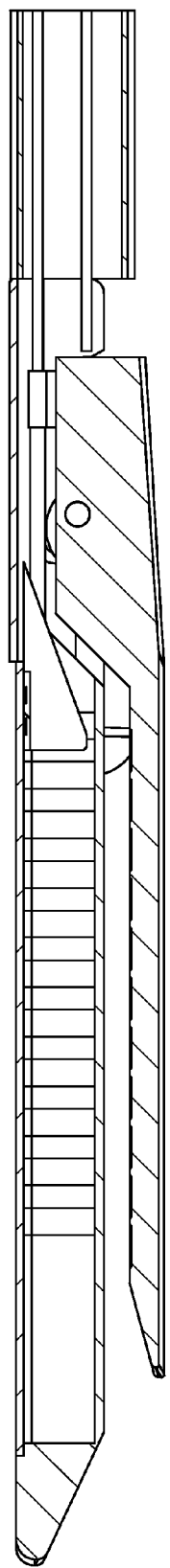
FIG. 29 is a vertical axial sectional view of the end effector with stapling completed and deployed blade nearly at an end of its travel and with cannula cutaway straight and staples and pushers hidden.
Figure 30:
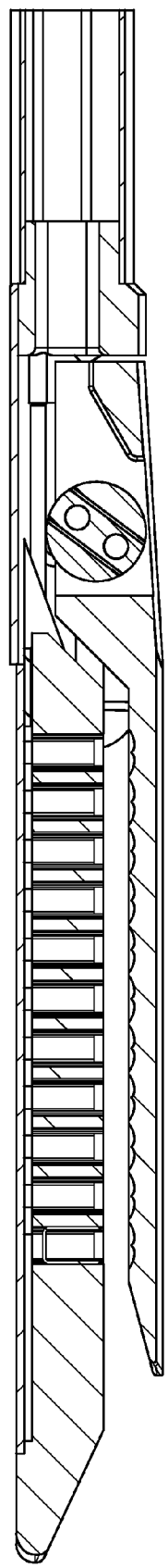
FIG. 30 is a view of the end effector in a fully fired condition with sled fully pulled and knife at the end of its range of motion.
Figure 32:
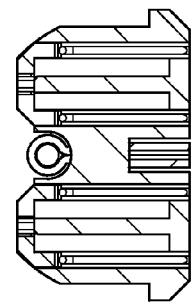
FIG. 32 is a transverse vertical sectional view of the cartridge of FIG. 31, taken along line 32-32.
Figure 31:
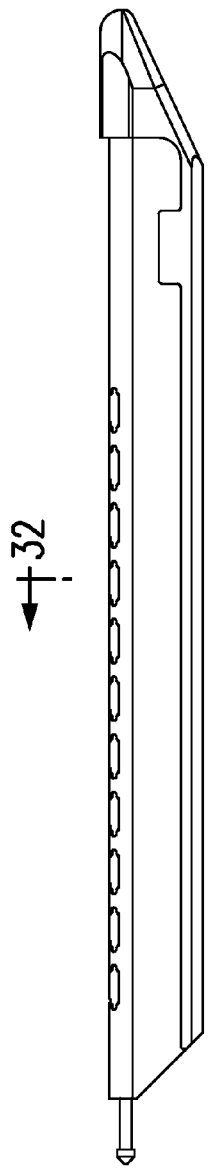
FIG. 31 is a side view of the staple cartridge.
Figure 33:
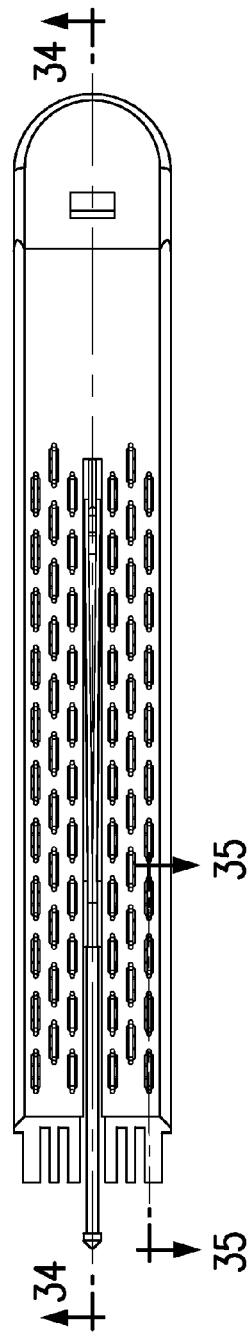
FIG. 33 is an underside view of the cartridge of FIG. 31.

As noted above, it may be desired to delay the cutting relative to the stapling. In the exemplary embodiment, this is achieved by coupling the blade puller to the ramp puller so that the ramp puller engages the blade puller only after the ramp puller has translated by a desired distance. In the exemplary implementation, this is achieved by allowing a dwell portion 320 (FIG. 18) of the ramp puller to freely pass through the second end portion 284 of the blade puller. Eventually, (e.g., immediately after the wedge fully forms a staple), at the end of a dwell interval (e.g., at least 1 mm, more particularly at least 10 mm, more particularly 15-40 mm or about 20 mm), a portion of the sled assembly will contact and engage the second end portion 284 so that the second end portion 286 is pulled along with the sled puller to initiate the cutting as is discussed above. In the exemplary embodiment, this may be achieved via a coil or other conduit 330 surrounding a portion of the sled puller near the sled (between the dwell portion and the sled). The exemplary conduit 330 has a first end 332 and a second end 334. The first end 332 comes into engagement with the puller first end 284 whereas the second end 334 engages the sled body flange in the start position. Upon contact of the end 332 with the knife puller, the knife will be drawn along with the sled, first deploying so that the cutting edge protrudes from the cartridge inboard face and then moving along with the sled to cut the tissue after the sled has caused stapling of the adjacent portions of the tissue to either side of the ultimate incision. The further drawing sheets respectively show: intermediate deployment of the knife with the cutting edge at approximately 45° to the cartridge inboard surface (FIGS. 22-25); a fully deployed blade near the beginning of its cutting range (FIGS. 26-28); with stapling completed and deployed blade nearly at an end of its travel (FIG. 29); and the fully deployed knife at the terminal end of its cutting range (FIG. 30).

The apparatus may be formed of appropriate conventional medical-grade materials (e.g., stamped and/or machined metals and molded and/or machined plastics) with parts formed and assemblies assembled via conventional techniques.

One or more embodiments of the present invention have been described. Nevertheless, it will be understood that various modifications may be made without departing from the spirit and scope of the invention. For example, if the principles are applied to the modification of an existing device, details of the existing device may influence the implementation. Additionally, details of any particular surgical operation may influence the properties of a device designed for such an operation. Accordingly, other embodiments are within the scope of the following claims.

What is claimed is:

1. A surgical stapler comprising:
   an end effector having:
   a staple cartridge holder; and
   an anvil movable relative to the staple cartridge holder between an open condition and a closed condition; and
   an actuator coupled to the end effector to actuate the end effector from the open condition to the closed condition and drive stapling,
   wherein:
   the actuator comprises:
   a handgrip body;
   a first lever pivotable relative to the handgrip body from an expanded condition to a contracted condition and coupled to the end effector so that rotation of the first lever from its expanded condition to its contracted condition drives the end effector from its open condition to its closed condition; and a second lever pivotable relative to the handgrip body between an expanded condition and a contracted condition and coupled to the end effector so that rotation of the second lever from its expanded condition to its contracted condition drives the stapling, wherein the first lever is behind the hand grip body and the second lever is in front of the hand grip body.

2. The stapler of claim 1 wherein:
the end effector has both stapling and cutting capability, and wherein
the second lever is coupled to the end effector so that rotation of the second lever from its expanded condition to its contracted condition drives a cutting.

3. The stapler of claim 1 wherein:
the first lever is pivotably mounted for rotation about a first axis and the second lever is pivotably mounted for rotation about a second axis parallel to the first axis.

4. The stapler of claim 1 wherein the actuator comprises:
a spring-loaded latch coupled to the first lever so that, upon the first lever reaching its contracted condition the latch prevents return of the first lever to its expanded condition; and
a latch release for disengaging the latch to permit return of the first lever to its expanded condition.

5. A surgical stapler comprising:
an end effector having:
a staple cartridge holder; and
an anvil movable relative to the staple cartridge holder between an open condition and a closed condition; and
an actuator coupled to the end effector to actuate the end effector from the open condition to the closed condition and drive stapling,
wherein:
the actuator comprises:
a handgrip body;
a first lever pivotable relative to the handgrip body from an expanded condition to a contracted condition and coupled to the end effector so that rotation of the first lever from its expanded condition to its contracted condition drives the end effector from its open condition to its closed condition; and
a second lever pivotable relative to the handgrip body between an expanded condition and a contracted condition and coupled to the end effector so that rotation of the second lever from its expanded condition to its contracted condition drives the stapling, wherein
the first lever is coupled to the end effector via a first flexible tension member and directly engages the first flexible tension member; and
the second lever is coupled to the end effector by a second flexible tension member and is coupled to the second flexible tension member by a ratio enhancement mechanism.

6. The stapler of claim 5 wherein:
the first flexible tension member comprises, at least along a portion engaging the end effector, a pair of flexible tension members laterally spaced from each other to prevent yawing torque.

7. A surgical stapler comprising:
an end effector having:
a staple cartridge holder; and
an anvil movable relative to the staple cartridge holder between an open condition and a closed condition; and
an actuator coupled to the end effector to actuate the end effector from the open condition to the closed condition and drive stapling,
wherein:
the actuator comprises:
a handgrip body;
a first lever pivotable relative to the handgrip body from an expanded condition to a contracted condition and coupled to the end effector so that rotation of the first lever from its expanded condition to its contracted condition drives the end effector from its open condition to its closed condition; and
a second lever pivotable relative to the handgrip body between an expanded condition and a contracted condition and coupled to the end effector so that rotation of the second lever from its expanded condition to its contracted condition drives the stapling, wherein
the first and second levers are respectively coupled to the end effector by first and second flexible tension members; and
the actuator is structurally coupled to the end effector via a conduit through which the first and second flexible tension members pass, the conduit positioned to undergo a counter-compression when tension is applied by the first and second triggers to the first and second flexible tension members.

8. A surgical stapler comprising:
an end effector having:
a staple cartridge holder; and
an anvil movable relative to the staple cartridge holder between an open condition and a closed condition; and
an actuator coupled to the end effector to actuate the end effector from the open condition to the closed condition and drive stapling,
wherein:
the actuator comprises:
a handgrip body;
a first lever pivotable relative to the handgrip body from an expanded condition to a contracted condition and coupled to the end effector so that rotation of the first lever from its expanded condition to its contracted condition drives the end effector from its open condition to its closed condition; and
a second lever pivotable relative to the handgrip body between an expanded condition and a contracted condition and coupled to the end effector so that rotation of the second lever from its expanded condition to its contracted condition drives the stapling, wherein, further comprising a blade cartridge in the cartridge holder, the blade cartridge comprising:
a cartridge body;
a plurality of staples, respectively accommodated in associated staple compartments of the cartridge body in an initial condition;
a plurality of staple pushers mounted in the body and positioned to be driven from an initial position to a second position, wherein movement from the initial position to the second position causes each staple pusher to drive one or more associated staples from their respective initial conditions outward toward fired conditions;
a sled positioned for a sliding movement along the body from an initial position to a second position and comprising:
a sled puller member having an end portion positioned so that pulling on the end portion tends to draw the sled from its initial position toward its second position; and a plurality of ramps positioned to sequentially essentially engage associated said staple pushers as the sled is drawn from its initial position toward its second position, the engagement of the ramps to the associated staple pushers depressing the associated staple pushers from their respective initial positions to their respective second positions and, thereby, progressively ejects associated said staples; and a knife assembly comprising;

a blade puller member having a first end portion through which the sled puller passes and a second end portion; and a blade mounted to the second end portion of the blade puller member and having a cutting edge.

9. The stapler of claim 8 wherein:

the blade is pivotally mounted to the blade puller; and the knife assembly has an initial position wherein the blade is accommodated in a blade compartment of the cartridge body and wherein a pulling of the slid puller member via the first end portion causes engagement between the blade and the surface of the blade compartment to rotate the blade to project the cutting edge from the cartridge body.

10. The stapler of claim 9 wherein:

the blade puller first end portion freely accommodates a dwell portion of the sled puller, whereby a pulling of the ramp puller from its first condition toward its second condition has:

an initial dwell phase wherein the dwell portion moves through the blade puller first portion without moving the blade; and a second phase wherein the dwell portion has passed through the first portion and a stop surface of the ramp puller engages the blade puller to, in turn, pull the blade assembly along with the ramp assembly.

11. The stapler of claim 8 wherein:

the cartridge body carries a first plurality of said staples on a first side of the knife assembly and a second plurality of said staples along a second side of the knife assembly, the first and second pluralities of staples each comprising a plurality of rows of said staples.

12. An end effector having:

a staple cartridge holder; and an anvil movable relative to the staple cartridge holder between an open condition and a closed condition; and an actuator coupled to the end effector to actuate the end effector from the open condition to the closed condition and drive stapling, wherein:

the actuator comprises:

a handgrip body;

a first lever pivotable relative to the handgrip body from an expanded condition to a contracted condition and coupled to the end effector so that rotation of the first lever from its expanded condition to its contracted condition drives the end effector from its open condition to its closed condition; and a second lever pivotable relative to the handgrip body between an expanded condition and a contracted condition and coupled to the end effector so that rotation of the second lever from its expanded condition to its contracted condition drives the stapling, wherein further comprising a blade cartridge in the cartridge holder, the blade cartridge comprising:

a cartridge body;

a plurality of staples, respectively accommodated in associated staple compartments of the cartridge body in an initial condition;

a plurality of staple pushers mounted in the body and positioned to be driven from an initial position to a second position, wherein movement from the initial position to the second position causes each staple pusher to drive one or more associated staples from their respective initial conditions outward toward fired conditions;

a sled positioned for a sliding movement along the body from an initial position to a second position to sequentially essentially engage associated said staple, the engagement of the ramps to the associated staple pushers depressing the associated staple pushers from their respective initial positions to their respective second positions and, thereby, progressively ejects associated said staples; and a knife assembly coupled to the sled so as to be pulled along with the sled after a dwell interval of motion of the sled.

13. The stapler of claim 12 wherein:

the dwell interval is at least 1 mm.

14. The stapler of claim 12 wherein:

a blade of the knife assembly is positioned to rotate into a deployed condition after said dwell.

\* \* \* \* \*